(12) United States Patent
Nickloes

(10) Patent No.: US 9,072,899 B1
(45) Date of Patent: Jul. 7, 2015

(54) DIAPHRAGM PACEMAKER

(76) Inventor: Todd Nickloes, Rockford, TN (US)

( * ) Notice: Subject to any disclaimer, the term of this patent is extended or adjusted under 35 U.S.C. 154(b) by 1303 days.

(21) Appl. No.: 12/874,323

(22) Filed: Sep. 2, 2010

Related U.S. Application Data

(60) Provisional application No. 61/239,806, filed on Sep. 4, 2009.

(51) Int. Cl.
*A61N 1/00* (2006.01)
*A61N 1/36* (2006.01)

(52) U.S. Cl.
CPC .................. *A61N 1/3601* (2013.01); *A61N 1/36* (2013.01)

(58) Field of Classification Search
CPC ............. A61N 1/36; A61N 1/18; A61N 1/00; A61N 1/08; A61B 5/00
USPC ........................................................... 607/42
See application file for complete search history.

(56) References Cited

U.S. PATENT DOCUMENTS

| | | | |
|---|---|---|---|
| 5,524,632 A * | 6/1996 | Stein et al. ..................... 600/546 |
| 5,716,385 A * | 2/1998 | Mittal et al. ..................... 607/40 |
| 6,198,952 B1 | 3/2001 | Miesel |
| 6,541,268 B1 * | 4/2003 | Tonnessen et al. ........... 436/133 |
| 6,600,949 B1 | 7/2003 | Turcott |
| 6,928,324 B2 | 8/2005 | Park et al. |
| 7,094,207 B1 | 8/2006 | Koh |
| 7,245,971 B2 | 7/2007 | Park et al. |
| 7,454,250 B1 | 11/2008 | Bjorling et al. |
| 7,469,697 B2 | 12/2008 | Lee et al. |
| 7,622,304 B2 | 11/2009 | Tonnessen et al. |
| 2006/0036294 A1 * | 2/2006 | Tehrani ........................... 607/42 |
| 2006/0282131 A1 | 12/2006 | Caparso et al. |

* cited by examiner

*Primary Examiner* — Christopher D Koharski
*Assistant Examiner* — Roland Dinga
(74) *Attorney, Agent, or Firm* — Luedeka Neely Group, P.C.

(57) ABSTRACT

The application describes a diaphragm pacemaker that uses an implanted $CO_2$ sensor to constantly monitor $CO_2$ in the body and adjust the pace of breathing based on the amount of $CO_2$. The sensor is preferably placed in tissue such as fat or muscle to sense $CO_2$. The $CO_2$ sensor and diaphragm pacemaker unit are preferably implanted in the shoulder or neck area so that the entire device may be implanted and connected to the body without invading the stomach or diaphragm area.

19 Claims, 4 Drawing Sheets

DIAPHRAGM PACEMAKER

CROSS-REFERENCE TO RELATED APPLICATION

This application claims priority to provisional application No. 61/239,806 filed Sep. 4, 2009 entitled Diaphragm Pacemaker, the entire contents being incorporated herein by reference.

FIELD OF THE INVENTION

This invention relates generally to diaphragmatic pacemakers for controlling the breathing of a patient. More specifically, this invention relates to a diaphragm pacemaker that uses an implanted $CO_2$ sensor to constantly monitor $CO_2$ in the body and adjust the pace of breathing based on the amount of $CO_2$. The sensor is preferably placed in tissue such as fat or muscle to sense $CO_2$.

BACKGROUND

Diaphragm pacemakers, also known as breathing pacemakers, are typically used in patients suffering from a variety of breathing diseases such as central sleep apnea, hypoventilation, and quadriplegia. In normal breathing patterns, we draw air into our lungs, oxygenate our blood via gas exchange in the alveoli, and exhale. Our respiratory rate automatically adjusts as the carbon dioxide and oxygen content in the blood changes. Accordingly, when there is a buildup of $CO_2$ levels in our blood and tissue, the central nervous system should automatically generate nerve signals to stimulate breathing. These nerve signals are relayed to the diaphragm and the chest wall muscles and collectively contract to expand the lungs. However, in individuals suffering from breathing diseases such as the diseases identified above, there is a breakdown in this respiratory process and the nerve signals are not properly generated or are of an insufficient magnitude to stimulate the breathing. Accordingly, diaphragm pacemakers provide an artificial means of inducing respiration.

Diaphragm pacemakers are implantable medical devices that stimulate the phrenic nerves in order to cause the contraction of the diaphragm in patients suffering from breathing diseases. In a basic system, a diaphragm pacemaker consists of a surgically implanted receiver and electrodes and an external transmitter that is connected to an antenna also worn outside the body. The external transmitter and antenna send radiofrequency energy to the implanted receiver. The receiver then converts the radio waves into stimulating pulses that are sent down the electrodes to the phrenic nerves causing the diaphragm to contract resulting in inhalation of air. When the pulses stop, the diaphragm relaxes and exhalation occurs. Repetition of this pattern produces a normal breathing pattern.

In traditional diaphragm pacemakers, the rate and duration of the pulses, which represent the respiratory rate and depth of inhalation, are fixed and do not vary with the ever changing physiological requirements of the body. To adjust the settings, a patient can be hooked up to a data transmitter to provide diagnostic monitoring of the diaphragm pacing equipment as well as the patient's physiological response to the stimulation. The data transmitter records and transmits the data so that a medical professional can determine whether the settings of the diaphragm pacemaker need to be adjusted.

It is also possible to control the pacing of the system using a pulse oximeter. A pulse oximeter is a medical device that indirectly measures the oxygen saturation of a patient's blood (as opposed to measuring oxygen saturation directly through a blood sample) and changes in blood volume in the skin, producing a photoplethysmograph (PPG). However, the use of pulse oximeters has its disadvantages, such as a patient could have excellent blood oxygen levels while still suffering from respiratory acidosis due to excessive carbon dioxide. Thus, it is necessary to also measure $CO_2$ levels.

Accordingly, it is desirable to provide for a more accurate and suitable manner in which to monitor and adjust the settings of a diaphragmatic pacemaker.

SUMMARY

The invention described herein pertains to a diaphragm pacemaker that uses an implanted $CO_2$ sensor to constantly monitor $CO_2$ in the body and adjust the pace of breathing based on the amount of $CO_2$. While the sensor could be placed in blood (this may cause health problems), the sensor is preferably placed in tissue such as fat or muscle to sense $CO_2$.

In one embodiment of the invention, a diaphragm pacemaker is disclosed for assisting the breathing of a patient. The diaphragm pacemaker includes a sensor unit configured to be implantable in the patient at a measurement site, the sensor unit for generating a plurality of carbon dioxide measurement signals representative of the amount of carbon dioxide at the measurement site. A pacemaker unit receives the plurality of carbon dioxide measurement signals from the sensor unit and delivers a plurality of stimulating pulses to a phrenic nerve of the patient based at least in part on the plurality of carbon dioxide measurement signals.

In another embodiment of the invention, a diaphragm pacemaker is disclosed having a sensor unit configured to be implantable in tissue of the patient at a measurement site, the sensor unit for generating a plurality of carbon dioxide measurement signals representative of the amount of carbon dioxide at the measurement site. A pacemaker unit receives the plurality of carbon dioxide measurement signals from the sensor unit and delivers a plurality of stimulating pulses to a phrenic nerve of the patient based at least in part on the carbon dioxide measurement signals. The pacemaker unit includes a resistance meter for measuring the plurality of carbon dioxide measurement signals received from the sensor unit and a controller for adjusting the delivery of the plurality of stimulating pulses to the phrenic nerve of the patient as a function of the measured carbon dioxide measurement signals. The controller may increase the delivery of the plurality of stimulating pulses when the measured carbon dioxide measurement signals are less than about 36 mmHG and decrease the delivery of the plurality of stimulating pulses when the measured carbon dioxide measurement signals are greater than about 44 mmHG.

In some embodiments, the sensor unit is configured to be implanted in tissue of the patient and to sense carbon dioxide in the tissue and the pacemaker unit is configured and sized to be implanted adjacent the measurement site which may be adjacent a shoulder of the patient. The diaphragm pacemaker may also include a second sensor unit configured to be implantable in a patient at a second measurement site, the sensor unit for generating a second plurality of carbon dioxide measurement signals representative of the amount of carbon dioxide at the second measurement site, the pacemaker unit for receiving the second plurality of carbon dioxide measurement signals from the second sensor unit and delivering the plurality of stimulating pulses based at least in part on at least one of the first and second plurality of carbon dioxide measurement signals.

In yet another embodiment of the invention, a method for controlling the pace of breathing of a patient is disclosed. The method includes: monitoring an amount of carbon dioxide in the patient at a measurement site using a sensor unit configured to be implantable in the patient at the measurement site; generating a plurality of carbon dioxide measurement signals representative of the amount of carbon dioxide at the measurement site; transmitting the plurality of carbon dioxide measurement signals from the sensor unit to a pacemaker unit; and delivering a plurality of stimulating pulses from the pacemaker unit to a phrenic nerve of the patient based on the carbon dioxide measurement signals. The method may also further include measuring continuously the plurality of carbon dioxide measurement signals received from the sensor unit; adjusting the delivery of the plurality of stimulating pulses to the phrenic nerve of the patient as a function of the measured carbon dioxide measurement signals; increasing the delivery of the plurality of stimulating pulses when the measured carbon dioxide measurement signals are less than about 36 mmHG; and decreasing the delivery of the plurality of stimulating pulses when the measured carbon dioxide measurement signals are greater than about 44 mmHG.

In some embodiments, the monitoring step includes monitoring the amount of carbon dioxide in tissue of the patient. The monitoring step may also include monitoring the amount of carbon dioxide in tissue adjacent a shoulder of the patient.

BRIEF DESCRIPTION OF THE DRAWINGS

Further advantages of the invention are apparent by reference to the detailed description in conjunction with the figures.

DETAILED DESCRIPTION

Figure 1:
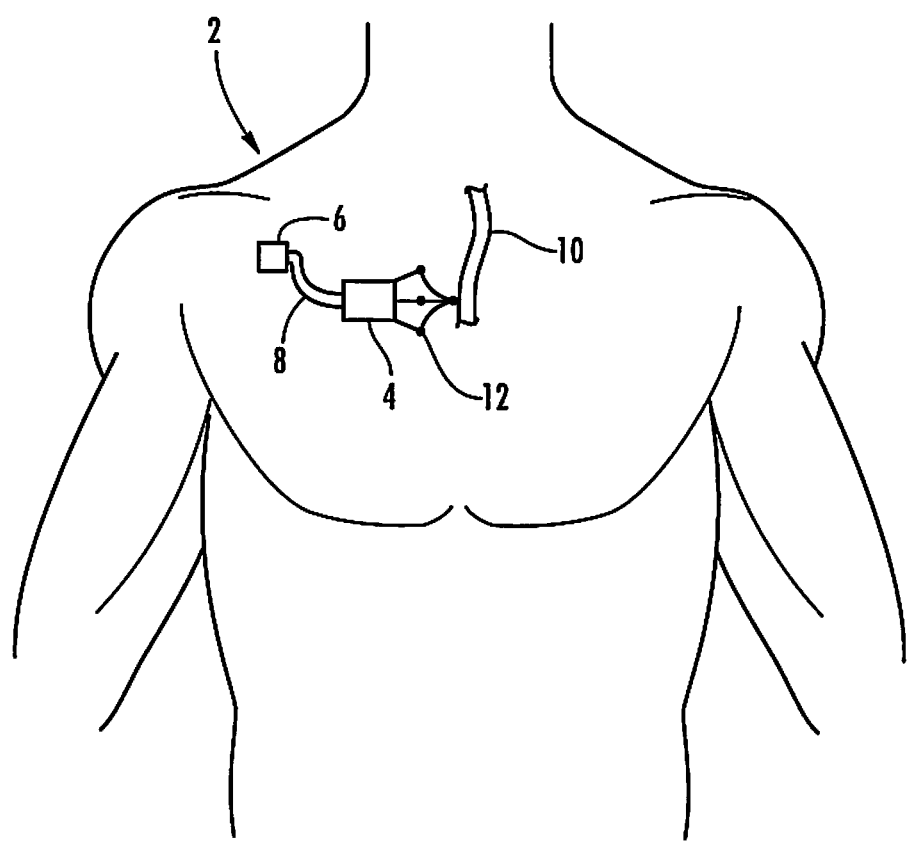
FIG. 1 depicts an implantable breathing system according to one embodiment of the present invention.

Referring to FIG. 1, an implantable breathing system 2 is illustrated. The implantable breathing system 2 includes a pacemaker unit 4 for stimulating breathing of a patient and a sensor unit 6 for monitoring the respiration of a patient by detecting $CO_2$ levels in the body. The pacemaker unit 4 receives the $CO_2$ information from the sensor unit 6 via electrical leads 8 and monitors the $CO_2$ information to control delivery of stimulating pulses to the phrenic nerves 10. The stimulating pulses are sent to the phrenic nerves 10 through nerve stimulating electrodes 12 connected to the pacemaker unit 4.

Figure 2:
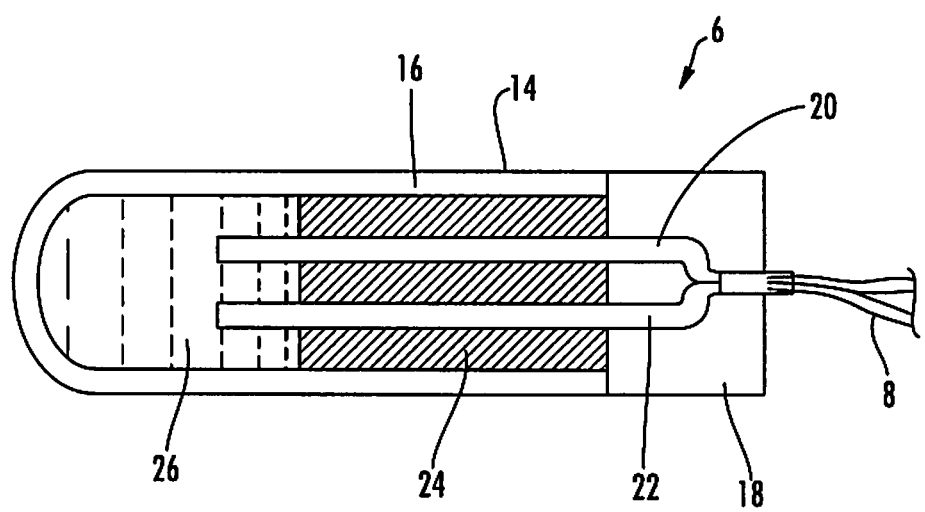
FIG. 2 depicts a cross-sectional view of a sensor unit for measuring $CO_2$ levels in tissue according to one embodiment of the invention.

Referring to FIG. 2, there is shown a sensor unit 6 that can be used in the present invention to determine $CO_2$ levels in tissue at a measurement site. The $CO_2$ sensor 6 includes a probe 14 having a carbon dioxide permeable membrane 16 located at the distal end and a cap 18 at the proximal end. Located within the housing are two electrodes 20 and 22 (e.g. carbon electrodes) and an insulated electrode holder 24. The measurement zone of the probe 14 distal end is filled with a substantially electrolyte-free liquid 26, preferably water, contacting the carbon dioxide permeable membrane 16 and the two electrodes 20 and 22. The two electrodes 20 and 22 are connected to the electrical leads 8 which pass through the cap 18 to the pacemaker unit 4. This sensor unit 6 is one example of a carbon dioxide sensor capable of sensing carbon dioxide in fat or other tissue of a human body, but other types and configurations of carbon dioxide sensors are known in the art and may be used.

Figure 3A:
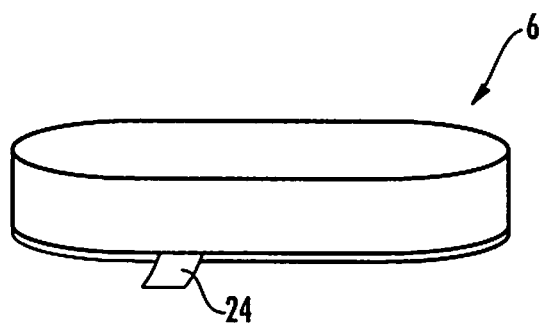
FIG. 3A depicts a sensor unit having a suture tab for attachment to tissue according to one embodiment of the invention.
Figure 3B:
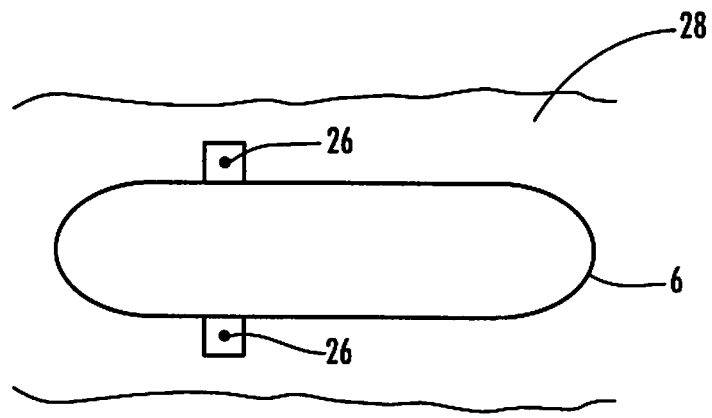
FIG. 3B depicts a top view of the sensor unit as shown in FIG. 3A.
Figure 3C:
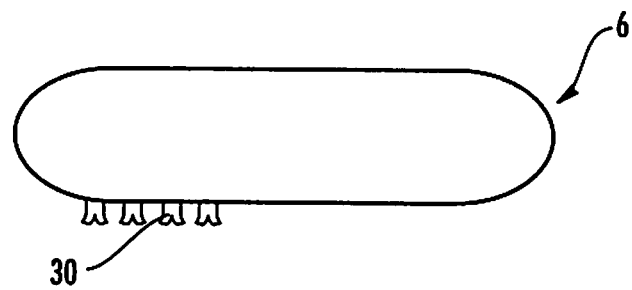
FIG. 3C depicts a sensor unit having a barb-like outer surface for attachment to tissue according to one embodiment of the invention.

In preferred embodiments, the sensor unit 6 is implanted in tissue near the shoulder or neck area adjacent the pacemaker unit 4 so that the entire device may be implanted in one area and to prevent invading the stomach or diaphragm area of the body. The sensor unit 6 may be attached to the surface of the tissue to determine the $CO_2$ levels of the monitoring site by providing the sensor unit 6 with various surface attachment means as exemplified in FIGS. 3A-3C. In FIG. 3A, an adjustable clip or suture tab 24 is provided for securing the sensor unit 6 to tissue. As shown in the top view of the suture tab 24 in FIG. 3B, the tab includes suture holes 26 for passing sutures through the tissue 28. In FIG. 3C, the sensor unit 6 includes a flexible barb-like outer surface 30 for attachment of the sensor unit 6 to the tissue. Other anchoring components may also be used such as hooks, clamps, prongs, etc. Alternatively, an incision may be provided for insertion of the sensor unit into the tissue. If desired, multiple $CO_2$ sensors units 6 may be used to measure $CO_2$ information from different measurement sites. While the preferred site for the sensor unit is the neck or shoulder, in certain patients it may be necessary or desirable to locate the device in other areas of the body, including the stomach and diaphragm areas, with electrical leads extending from the device to the appropriate nerves for controlling breathing.

The sensor unit 6 of the invention is connected to an AC electrical power source that will apply an alternating electrical potential across the electrodes 20 and 22 with a frequency of 20 to 10000 Hz. The electrical power may be provided by the pacemaker unit 4. In alternate embodiments, the sensor unit 6 may provide for its own power source such as a battery. The sensor unit 6 operates to measure $CO_2$ levels in the tissue because the addition of $CO_2$ passing through the membrane to the electrolyte-free liquid 26 (e.g. water) results in formation of $H^+$ and $HCO^-_3$ ions and thus a reduction in the electrical resistance. Because the only significant factor responsible for the reduction in the electrical resistance in the sensor unit 6 is $CO_2$ passing through the membrane 16, the change in resistance allows $CO_2$ to be measured.

Figure 4:
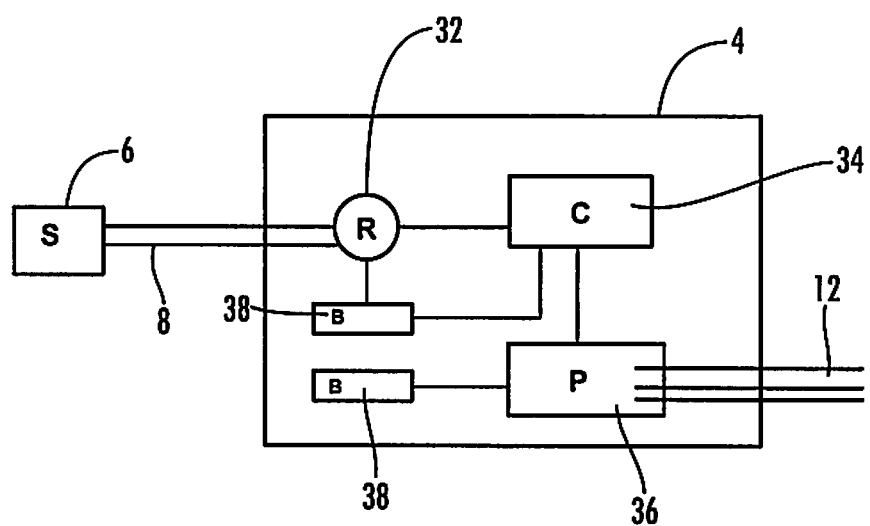
FIG. 4 depicts a circuit diagram of the implantable breathing system according to one embodiment of the present invention.

Referring to FIG. 4, the pacemaker unit 4 includes a resistance meter 32 and a controller 34. The resistance meter 32 is connected to the electrical leads 8 of the sensor unit 6 for continually measuring the $CO_2$ levels in the tissue of the measurement site or sites. The $CO_2$ information is then delivered to a controller 34 which determines the delivery of the stimulation to the phrenic nerves 10 based on the $CO_2$ information transmitted from the sensor unit 6. Stimulating pulses are then sent from a power output device 36 of the pacemaker unit 4 through the electrodes 12 to the phrenic nerves 10 causing the patient's diaphragm to contract and breathing to occur. Thus, the controller 34 adjusts the pace of breathing of the patient by controlling the rate and duration of the stimulating pulses delivered by the power output device 36.

In preferred embodiments, the controller 34 adjusts the pace of breathing as a function of the measured $PCO_2$ levels in the tissue of the measurement site by increasing or decreasing the rate of contraction of the patient's diaphragm when the PCO₂ measurements fall outside a target range. In typical patients, the target range for PCO₂ should be between about 38 mmHG to 42 mmHG, with 40 mmHG generally being ideal. Using this target range as an example, the rate of contraction of the patient's diaphragm may be increased or decreased by the controller 34 based on the measurements recorded by the resistance meter 32 based on the following exemplary formula:

PCO₂=37: increase rate of contraction by 1 breath/minute;
PCO₂=36: increase rate of contraction by 2 breaths/minute;
PCO₂=35: increase rate of contraction by 2 breaths/minute;
PCO₂=34: increase rate of contraction by 2 breaths/minute;
PCO₂=33: increase rate of contraction by 3 breaths/minute;
PCO₂=32: increase rate of contraction by 3 breaths/minute;
PCO₂=30: increase rate of contraction by 3 breaths/minute; and
PCO₂<30: increase rate of contraction by 4 breaths/minute.
PCO₂=43: decrease rate of contraction by 1 breath/minute;
PCO₂=44: decrease rate of contraction by 2 breaths/minute;
PCO₂=45: decrease rate of contraction by 2 breaths/minute;
PCO₂=46: decrease rate of contraction by 2 breaths/minute;
PCO₂=47: decrease rate of contraction by 3 breaths/minute;
PCO₂=49: decrease rate of contraction by 3 breaths/minute;
PCO₂=50: decrease rate of contraction by 3 breaths/minute; and
PCO₂>50: decrease rate of contraction by 4 breaths/minute.

While the above formula for controlling the breathing of the patient is provided as an example, a doctor or other healthcare professional may change the settings of the pacemaker unit 4 to alter the rate of rate of contraction of the diaphragm based on the needs of each particular patient. Furthermore, the doctor or patient may establish a particular CO₂ level in which the pacemaker unit 4 provides an alarm to the patient or medical staff that the patient's CO₂ level has risen or dropped above a critical level. For example, an alarm signal may be produced by the pacemaker unit 4 whenever the PCO₂ measurement is below 30 mmHG or above 50 mmHG.

As shown in FIG. 4, the pacemaker unit 4 may be powered by providing at least one battery 38. Preferably, the battery or batteries 38 are rechargeable and may be recharged through the patient's skin via induction coils. Alternatively, the implanted breathing system 2 may be powered by providing an external power transmitter.

Accordingly, an implantable breathing system is disclosed in which an implanted CO₂ sensor is placed in or on the surface of tissue such as fat or muscle. The sensor is connected to a diaphragm pacemaker having a controller that may constantly monitor CO₂ levels of the tissue and may adjust the pace of breathing based on the CO₂ information gathered by the sensor.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention.

What is claimed is:

1. A diaphragm pacemaker for assisting the breathing of a patient, the diaphragm pacemaker comprising:
    a sensor unit configured to be implantable in the patient at a measurement site, the sensor unit for generating a plurality of carbon dioxide measurement signals representative of the amount of carbon dioxide at the measurement site; and
    a pacemaker unit for receiving the plurality of carbon dioxide measurement signals from the sensor unit and for delivering a plurality of stimulating pulses to a phrenic nerve of the patient based at least in part on the plurality of carbon dioxide measurement signals.

2. The diaphragm pacemaker of claim 1 wherein the sensor unit is configured to be implanted in tissue of the patient and to sense carbon dioxide in the tissue.

3. The diaphragm pacemaker of claim 1 wherein the pacemaker unit is configured and sized to be implanted adjacent the measurement site.

4. The diaphragm pacemaker of claim 3 wherein the sensor unit and pacemaker unit are configured and sized to be implanted adjacent a shoulder of the patient.

5. The diaphragm pacemaker of claim 1 further comprising a second sensor unit configured to be implantable in a patient at a second measurement site, the second sensor unit for generating a second plurality of carbon dioxide measurement signals representative of the amount of carbon dioxide at the second measurement site, the pacemaker unit for receiving the second plurality of carbon dioxide measurement signals from the second sensor unit and delivering the plurality of stimulating pulses based at least in part on at least one of the first and second plurality of carbon dioxide measurement signals.

6. The diaphragm pacemaker of claim 1 wherein the pacemaker unit further comprises:
    a resistance meter for continually measuring the plurality of carbon dioxide measurement signals received from the sensor unit; and
    a controller for adjusting the delivery of the plurality of stimulating pulses to the phrenic nerve of the patient as a function of the measured carbon dioxide measurement signals.

7. The diaphragm pacemaker of claim 6 wherein the controller increases the delivery of the plurality of stimulating pulses when the measured carbon dioxide measurement signals are less than about 36 mmHG and decreases the delivery of the plurality of stimulating pulses when the measured carbon dioxide measurement signals are greater than about 44 mmHG.

8. The diaphragm pacemaker of claim 6 wherein the pacemaker unit generates an alarm signal when the measured carbon dioxide measurement signal has reached a critical level.

9. A diaphragm pacemaker for assisting the breathing of a patient, the diaphragm pacemaker comprising:
    a sensor unit configured to be implantable in tissue of the patient at a measurement site, the sensor unit for generating a plurality of carbon dioxide measurement signals representative of the amount of carbon dioxide at the measurement site; and a pacemaker unit for receiving the plurality of carbon dioxide measurement signals from the sensor unit and for delivering a plurality of stimulating pulses to a phrenic nerve of the patient based at least in part on the carbon dioxide measurement signals, the pacemaker unit including:
- a resistance meter for measuring the plurality of carbon dioxide measurement signals received from the sensor unit;
- a controller for adjusting the delivery of the plurality of stimulating pulses to the phrenic nerve of the patient as a function of the measured carbon dioxide measurement signals.

10. The diaphragm pacemaker of claim 9 wherein the pacemaker unit is configured and sized to be implanted adjacent the measurement site.

11. The diaphragm pacemaker of claim 9 wherein the sensor unit and pacemaker unit are configured and sized to be implanted adjacent a shoulder of the patient.

12. The diaphragm pacemaker of claim 9 wherein the controller increases the rate delivery of the plurality of stimulating pulses when the measured carbon dioxide measurement signals are less than about 36 mmHG and decreases the rate of delivery of the plurality of stimulating pulses when the measured carbon dioxide measurement signals are greater than about 44 mmHG.

13. The diaphragm pacemaker of claim 9 further comprising a second sensor unit configured to be implantable in a patient at a second measurement site, the second sensor unit for generating a second plurality of carbon dioxide measurement signals representative of the amount of carbon dioxide at the second measurement site, the pacemaker unit for receiving the second plurality of carbon dioxide measurement signals from the second sensor unit and delivering the plurality of stimulating pulses based at least in part on at least one of the first and second plurality of carbon dioxide measurement signals.

14. A method for controlling the pace of breathing of a patient, the method comprising:
- monitoring an amount of carbon dioxide in the patient at a measurement site using a sensor unit configured to be implantable in the patient at the measurement site;
- generating a plurality of carbon dioxide measurement signals representative of the amount of carbon dioxide at the measurement site;
- transmitting the plurality of carbon dioxide measurement signals from the sensor unit to a pacemaker unit; and
- delivering a plurality of stimulating pulses from the pacemaker unit to a phrenic nerve of the patient based at least in part on the carbon dioxide measurement signals.

15. The method of claim 14 further comprising:
- measuring continuously the plurality of carbon dioxide measurement signals received from the sensor unit; and
- adjusting the delivery of the plurality of stimulating pulses to the phrenic nerve of the patient as a function of the measured carbon dioxide measurement signals.

16. The method of claim 15 further comprising:
- increasing the rate of delivery of the plurality of stimulating pulses when the measured carbon dioxide measurement signals are less than about 36 mmHG; and
- decreasing the rate of delivery of the plurality of stimulating pulses when the measured carbon dioxide measurement signals are greater than about 44 mmHG.

17. The method of claim 14 wherein the monitoring step comprises monitoring the amount of carbon dioxide in tissue of the patient.

18. The method of claim 14 wherein the monitoring step comprises monitoring the amount of carbon dioxide in tissue adjacent a shoulder of the patient.

19. The method of claim 14 further comprising:
- monitoring an amount of carbon dioxide in the patient at a second measurement site using a second sensor unit implantable in the patient at the second measurement site;
- generating a second plurality of carbon dioxide measurement signals representative of the amount of carbon dioxide at the second measurement site;
- transmitting the second plurality of carbon dioxide measurement signals from the second sensor unit to the pacemaker unit; and
- delivering a plurality of stimulating pulses from the pacemaker unit to a phrenic nerve of the patient based on the first and second plurality of carbon dioxide measurement signals.

* * * * *